US010048391B2

(12) United States Patent
Steadman Booker et al.

(10) Patent No.: US 10,048,391 B2
(45) Date of Patent: Aug. 14, 2018

(54) IMAGING DETECTOR SELF-DIAGNOSIS CIRCUITRY

(71) Applicant: KONINKLIJKE PHILIPS N.V., Eindhoven (NL)

(72) Inventors: Roger Steadman Booker, Aachen (DE); Gereon Vogtmeier, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 296 days.

(21) Appl. No.: 15/100,659

(22) PCT Filed: Nov. 21, 2014

(86) PCT No.: PCT/IB2014/066224
§ 371 (c)(1),
(2) Date: Jun. 1, 2016

(87) PCT Pub. No.: WO2015/083031
PCT Pub. Date: Jun. 11, 2015

(65) Prior Publication Data
US 2016/0306053 A1     Oct. 20, 2016

Related U.S. Application Data

(60) Provisional application No. 61/911,622, filed on Dec. 4, 2013.

(51) Int. Cl.
*G01T 1/24*     (2006.01)
*G01T 1/164*     (2006.01)
(Continued)

(52) U.S. Cl.
CPC ............ *G01T 1/247* (2013.01); *A61B 6/032* (2013.01); *G01T 1/1648* (2013.01); *G01T 1/2018* (2013.01)

(58) Field of Classification Search
CPC .......... G01T 1/247; G01T 1/2018; G01T 1/24; H04N 5/32
See application file for complete search history.

(56) References Cited

U.S. PATENT DOCUMENTS 6,488,409 B1   12/2002   Vafi et al.
6,671,345 B2   12/2003   Vrettos et al.
(Continued)

FOREIGN PATENT DOCUMENTS

WO     2005/040855     5/2005

OTHER PUBLICATIONS

Luhta, et al., "A New 2D-Tiled Detector for Multislice CT", Proc. SPIE 6142, Medical Imaging 2006: Physics of Medical Imaging, 61420U (Mar. 2, 2006).
(Continued)

*Primary Examiner* — Don Wong

(57) ABSTRACT

An imaging detector module (112) of an imaging system includes at least one detector pixel (114) and self-diagnosing circuitry (116). The self-diagnosing circuitry includes a microprocessor (202) and at least measurement device (210). The microprocessor controls the at least measurement device to measure at least one parameter of the at least one detector pixel, wherein a value of the at least one parameter is indicative of a health state of the imaging system. A method includes employing self-diagnosing circuitry embedded in an imaging detector module to measure at least one parameter of at least one detector pixel of the imaging detector module. A value of the at least one parameter is indicative of a health state of the imaging detector. The method further includes generating, with the self diagnosing circuitry, a signal indicating a health state of the imaging detector module based on the measured at least one parameter.

18 Claims, 4 Drawing Sheets

(51) Int. Cl.
*G01T 1/20* (2006.01)
*A61B 6/03* (2006.01)

(56) References Cited

U.S. PATENT DOCUMENTS

| | | |
|---|---|---|
| 2006/0149808 A1 | 7/2006 | Weiner et al. |
| 2008/0298541 A1 | 12/2008 | Mattson et al. |
| 2010/0076729 A1 | 3/2010 | Davis et al. |
| 2011/0073769 A1* | 3/2011 | Enomoto ................ 250/370.08 |
| 2013/0062525 A1 | 3/2013 | Caruba |

OTHER PUBLICATIONS

Jungman, et al., "An in-vacuum, pixelated detection system for mass spectrometric analysis and imaging of macromolecules", International Journal of Mass Spectrometry, vol. 341-342, Mar. 4, 2013.

* cited by examiner

IMAGING DETECTOR SELF-DIAGNOSIS CIRCUITRY

CROSS REFERENCE TO RELATED APPLICATIONS

This application is the U.S. National Phase application under 35 U.S.C. § 371 of International Application No. PCT/IB2014/066224, filed Nov. 21, 2014, published as WO 2015/083031 on Jun. 11, 2015, which claims the benefit of U.S. Provisional Patent Application No. 61/911,622 filed Dec. 4, 2013. These applications are hereby incorporated by reference herein.

The following generally relates to an imaging detector and more particularly to self-diagnostic circuitry embedded in the imaging detector that monitors and reports on a current health state of the imaging detector, and is described with particular application to computed tomography (CT). However, the following is also amenable to other imaging modalities such as digital x-ray and/or other imaging modalities.

A CT scanner includes an x-ray tube that emits radiation that traverses an examination region. A detector array is located opposite the examination region across from the x-ray tube. The detector array includes detector modules, and each detector module includes detector pixels. Each detector pixel detects radiation traversing the examination region and generates a signal indicative thereof. A reconstructor processes the signals and generates volumetric image data indicative of the scanned examination region.

The lifetime of a detector module depends on factors such as radiation damage, packaging stability, etc. Some of these factors show a steady degradation in performance over time. In the case of radiation damage, for example, charge trapping can cause bias circuits of a detector module to shift their operating point beyond predefined limits, which can eventually yield to malfunction or compromised performance. This may be of particular importance in CT, as edge detector modules see more radiation than center detector modules.

The detector modules periodically undergo routine calibration (e.g., at the beginning of the day before the first procedure, etc.) to compensate for any drifts that may cause image artifacts. The calibration procedure attempts to ensure good image quality. Software based corrections can be used to correct for one or more inoperable or defective detector pixels, for example, by interpolating measurements of neighboring detectors pixels and replacing the value for the defective detector pixel with the interpolated value.

Unfortunately, there is limit as to what can be corrected and to what extent. For example, radiation damage can cause noise that may not limit the image quality in some procedures but may become an issue in low dose protocols (e.g., where the noise floor is raised, etc.), which are more susceptible to noise. Thus, there is an unresolved need for other approaches for monitoring a health state of a detector module.

Aspects described herein address the above-referenced problems and others.

The following describes an approach in which a detector module of a detector array includes at least one self-diagnosing circuit. The at least one self-diagnosing circuit monitors a predetermined set of parameters having known normal operational values. The at least one self-diagnosing circuit, based on the monitoring, provides information that facilitates scheduling service such as detector repair, replacement, calibration, software correction, etc. The provided information may indicate a current issue that needs attention and/or estimates when service will likely be required. In one instance, this allows for planning service and maximizing up time.

In one aspect, an imaging detector module of an imaging system includes at least one detector pixel and self-diagnosing circuitry. The self-diagnosing circuitry includes a microprocessor and at least one measurement device. The microprocessor controls the at least measurement device to measure at least one parameter of the at least one detector pixel, wherein a value of the at least one parameter is indicative of a health state of the imaging system.

In another aspect, a method includes employing self-diagnosing circuitry embedded in an imaging detector module of an imaging system to measure at least one parameter of at least one detector pixel of the imaging detector module. A value of the at least one parameter is indicative of a health state of the imaging detector. The method further includes generating, with the self-diagnosing circuitry, a signal indicating a health state of the imaging detector module based on the measured at least one parameter.

In another aspect, a computed tomography imaging system includes a console that controls a scanning operation of the imaging system. The computed tomography imaging system further includes a radiation source that emits radiation traversing an examination region. The computed tomography imaging system further includes detector array that detects radiation traversing the examination region. The detector array includes a detector module. The detector module includes at least one detector pixel and self-diagnosing circuitry. The self-diagnosing circuitry measures at least one parameter of the at least one detector pixel, generates imaging detector service related information for the imaging detector based on the measured at least one parameter, generates a signal including the information, and conveys the signal to the console, which visually displays a notification including the information.

The invention may take form in various components and arrangements of components, and in various steps and arrangements of steps. The drawings are only for purposes of illustrating the preferred embodiments and are not to be construed as limiting the invention.

FIG. 1 schematically illustrates an example imaging system with a detector module with self-diagnostic circuitry.

FIG. 2 schematically illustrates an example of the self-diagnostic circuitry.

FIG. 3 schematically illustrates a variation of the self-diagnostic circuitry of FIG. 2.

Figure 1:
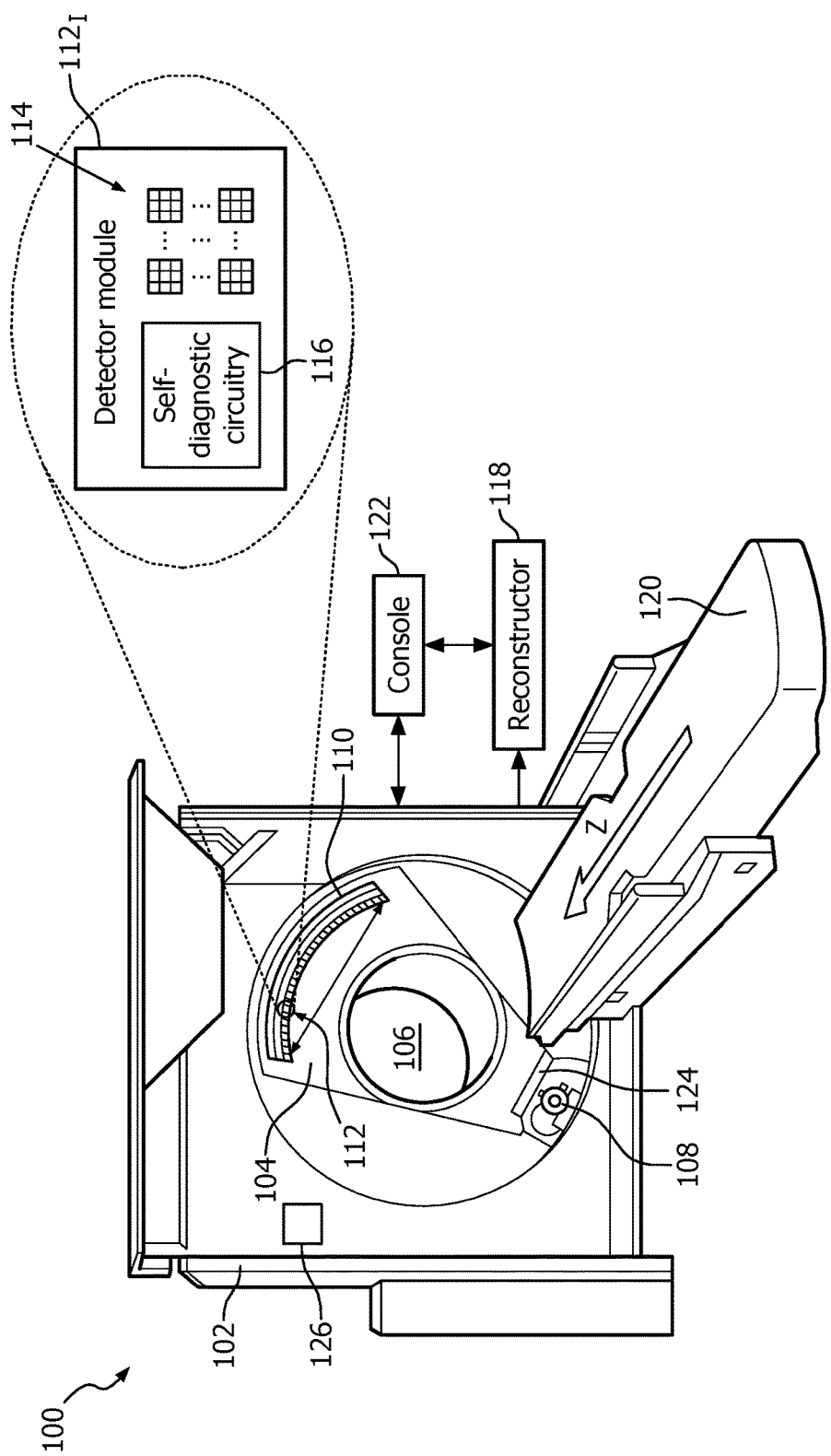

Initially referring to FIG. 1, an imaging system 100 is illustrated. In this example, the imaging system 100 is a computed tomography (CT) scanner.

The illustrated imaging system 100 includes a stationary gantry 102 and a rotating gantry 104, which is rotatably supported by the stationary gantry 102. The rotating gantry 104 rotates around an examination region 106 about a longitudinal or z-axis ("Z").

A radiation source 108, such as an x-ray tube, is supported by the rotating gantry 104 and rotates with the rotating gantry 104 about the examination region 106, and emits radiation that traverses the examination region 106.

A radiation sensitive imaging detector array 110 is located opposite the radiation source 108 across the examination region 106. The radiation sensitive imaging detector array 110 includes a plurality of detector modules 112, each including a two-dimensional (2D) array of detector pixels 114. The detector pixels 114 detect radiation traversing the examination region 106 and generate signals indicative thereof.

The plurality of detector modules 112 may include at least one integrating detector pixels, with a scintillator optically coupled to a photosensor and integrating circuitry. Alternatively, the plurality of detector modules 112 includes direct conversion or photon counting detector pixels, with a direct conversion material (e.g., CdTe, CdZnTe, etc.) and pulse shaping and counting circuitry. In yet another instance, the plurality of detector pixels 112 includes a combination of integrating and direct conversion detector pixels.

At least one of the detector modules 112 (a detector module $112_I$ in the illustrated example) includes self-diagnostic circuitry 116 embedded therein. In one instance, the self-diagnostic circuitry 116, is implemented with hardware, some of which stores and/or executes computer readable instructions. As described in greater detail below, in one non-limiting instance, the self-diagnostic circuitry 116 at least monitors a pre-determined set of parameters of the detector module $112_I$ that provides information that indicates a health state of the detector module 114.

The pre-determined set of parameters, generally, includes parameters that have known normal operating values, which change in a known manner in response to a degradation in the health of the detector module $112_I$ that leads to a degradation in imaging performance. Examples of suitable parameters that are monitored include, but are not limited to, detector bias current, detector dark current, detector gain, detector noise, detector sensitivity, detector homogeneity, detector crosstalk, and detector temperature.

As further described in greater detail below, the self-diagnosing circuitry 116 provides, based on the monitoring and an analysis thereof, information that facilitates scheduling service such as detector repair, detector replacement, detector calibration, detector output signal correction, etc. This may include setting one or more bits in a register, generating an estimated service date, etc. The monitoring and reporting can be performed on an individual detector pixel basis, a group of detector pixel in an individual module basis, an individual module basis, a group of modules basis, a detector array basis, and/or otherwise.

In a variation, at least one of the parameters of the pre-determined set of parameters of the detector module $112_I$ is conveyed from the detector module $112_I$ to a signal processor located remote from the detector module $112_I$. In this variation, the signal processor processes the at least one of the parameters and provides, based on a result of the processing, information that facilitates scheduling service such as detector repair, detector replacement, detector calibration, detector output signal correction, etc.

A reconstructor 118 reconstructs the signal generated by the radiation sensitive detector array. The reconstructor 118 can employ various reconstruction algorithms such as filtered back projection (FBP), iterative reconstruction, and/or other reconstruction algorithm.

A support 120 supports an object or subject in the examination region 106. The subject support 120 is movable in coordination with performing an imaging procedure so as to guide the subject or object with respect to the examination region 106 for loading, scanning, and/or unloading the subject or object.

A computer serves as an operator console 122 and includes an output device such as a display and an input device such as a keyboard, mouse, etc. Software resident on the console 122 allows the operator to control an operation of the system 100. In one instance, the software resident also includes a self-diagnostic software application. The self-diagnostic software application, in one instance, visually displays the information provided by and/or obtained from the self-diagnosing circuitry 116 and/or information derived there from.

The console 122 may display a notification (in human readable format) indicating service for and/or a health state of the detector module $112_I$ (e.g., re-calibration and/or replacement, degradation of performance, lifetime issues, defect, etc.). The notification may also include the particular measured parameter, along with the measured value and/or a trend of the measured value and an acceptable range for the parameter. The application may also send a service request, e.g., over a network, to a remote service computer, in response thereto.

Figure 2:
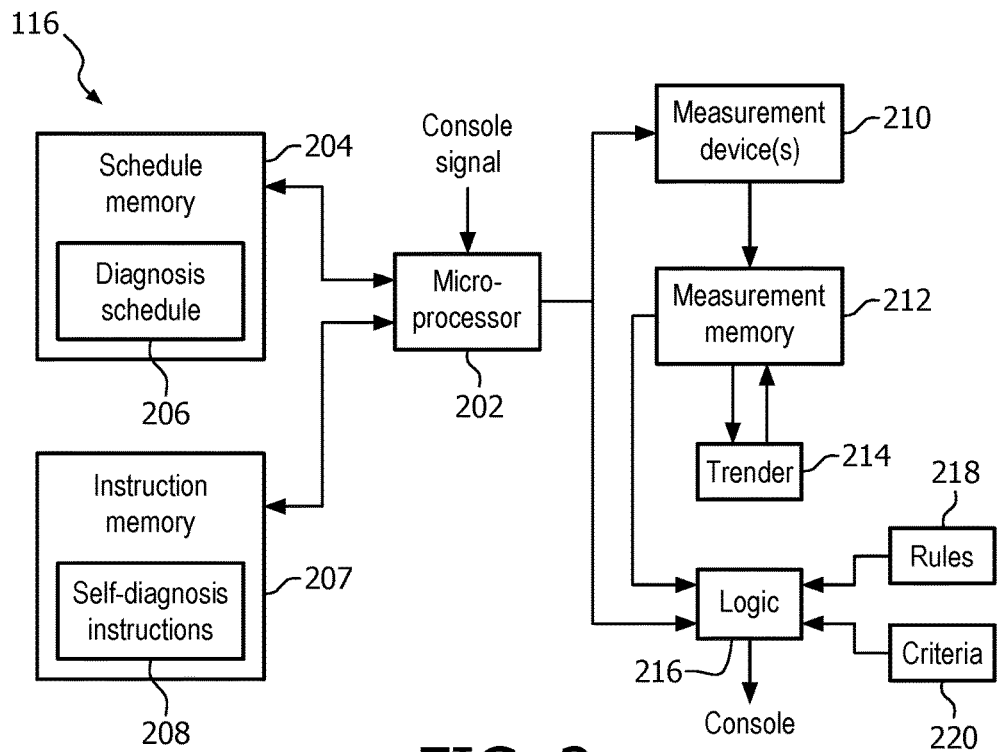

FIG. 2 schematically illustrates an example of the self-diagnostic circuitry 116.

The self-diagnosing circuitry 116 includes a microprocessor 202. The microprocessor 202 controls the self-diagnostic circuitry 116. In the illustrated embodiment, the console 122 (FIG. 1) conveys a signal to the microprocessor 202 that either invokes the microprocessor 202 to perform self-diagnostics or places the microprocessor 202 in an idle or sleep state. The signal, in one instance, is conveyed in response to a loading of a configuration or preferences file. In a variation, the signal is conveyed in response to a user input to the console 122 that activates self-diagnosis. In yet another instance, the signal is conveyed in response to a remote service request that activates self-diagnosis.

The self-diagnostic circuitry 116 further includes a schedule memory 204 which stores a diagnosis schedule 206. The microprocessor 202 invokes self-diagnosis based on the diagnosis schedule 206. In the illustrated example, the diagnosis schedule 206 is preloaded in the schedule memory 204. The diagnosis schedule 206 can be preloaded through application software running on the console 122, directly programming the schedule memory 204 through a physical electro-mechanical interface of the detector module 112, etc. The stored diagnosis schedule 206 can be modified, overwritten, overridden (e.g., by an on demand local and/or remote request), etc.

In one instance, the diagnosis schedule 206 includes separate schedules for self-diagnosing for at least two different parameters. Thus, one parameter may be measured at a given point in time whereas another parameter may not be measured at the same point in time. Furthermore, the diagnosis schedule 206 can be time and/or use based. For example, the diagnosis schedule 206 may indicate that a particular parameter be measured at the beginning, end and/or other time of a day, before, during and/or after scanning, once a month, in response to a predetermined event, etc. In one instance, the measurement is taken only during a time period(s) in which the measurement does not interfere with a diagnostic imaging operation such as during one or more idle times of the detector/scanner. In another instance, a diagnostic imaging operation is paused or delayed for a measurement.

The self-diagnostic circuitry 116 further includes an instruction memory 207 which stores self-diagnostic instructions 208. The microprocessor 202 controls the self-diagnosing circuitry 116 following the self-diagnosis instructions 208. Likewise, the self-diagnostic instructions 208 can be preloaded through application software running on the console 122, directly programming the instruction memory 207 through a physical electro-mechanical interface of the detector module 112, etc. The stored self-diagnostic instructions 208 also can be modified, overwritten, etc.

The self-diagnostic circuitry 116 further includes one or more measurement devices 210. The one or more measurement devices 210 measure the pre-determined set of parameters. The one or more measurement devices 210 are configured to measure at least one of a detector pixel bias current a detector pixel dark current, a detector pixel temperature and a detector pixel gain. The one or more measurement devices 210 can also measure one or more other parameters. Furthermore, a single one of the one or more measurement devices 210 measure one or more of the parameters.

With respect to a detector pixel bias current, radiation damage, e.g., can cause charge trapping, which can cause the bias current to shift its operating point, which can eventually yield to malfunction or compromised performance. Examples of a detector bias circuit are described in U.S. Pat. No. 6,671,345 B2 to Vrettos et al., filed Nov. 7, 2001, and entitled "Data Acquisition for Computed Tomography," which is incorporated herein by reference in its entirety, and "A New 2D-Tiled Detector for Multislice CT," Luhta et al., Medical Imaging 2006: Physics of Medical Imaging, Vol. 6142, pp. 275-286 (2006).

In the '345 patent and Luhta et al., the A/D converter includes an integrator that integrates, each integration period, an electrical current produced by a detector pixel in response to radiation impinging on the detector pixel. The integrator also integrates, each integration period, a bias current supplied to the integrator supplied by a bias current source. The one or more measurement devices 210 can measure this (or other) bias current by electrically decoupling the bias current source from the integrator and measuring the bias current with a bias current sensor of the one or more measurement devices 210.

Generally, the dark current is a relatively small electric current that flows through photodiode even when no radiation is impinging the detector. The dark current may partially discharge the bias current supplied to the A/D converter integrator, which introduces an offset into the output of the integrator. The one or more measurement devices 210 can measure the dark current when radiation source is "off" (or not emitting radiation) or otherwise not impinging the detector module with a dark current sensor of the one or more measurement devices 210.

With respect to temperature, the response of a detector pixel is sensitive to and may vary with temperature, and, unfortunately, temperature variations in the detector module may result in artifacts being introduced into the image data. An example approach for measuring detector temperature is described in U.S. Pat. No. 8,405,040 to Luhta et al., filed on Aug. 10, 2010, and entitled "Imaging detector thermal control," the entirety of which is incorporated herein by reference. In the '040 patent, the detector includes a plurality of temperature sensors that sense temperatures at different locations of the detector. The one or more measurement devices 210 can measure the detector module temperature using one of these and/or temperature sensor of the one or more measurement devices 210.

Detector gain generally refers to the ratio of the output to the input of the detector. The detector gain can drift over time, which can compromise image quality. The drift can be compensated for through calibration. An initial airscan (a scan in which no object or subject in the examination region 106) is performed at the time of calibration and used to calibrate the detector gain. If the detector gain does not drift, the detector output of a subsequent airscan will be approximate the same as the output of the calibrated detector. However, if the detector gain drifts, the detector output will be different. The one or more measurement devices 210 can measure the output from different airscans.

The self-diagnostic circuitry 116 further includes measurement memory 212, which stores the measured parameters. The measured parameters include measured parameters acquired during imaging system calibration (e.g., minimum and/or maximum values) and measured parameters acquired during self-diagnosis. The self-diagnosing circuitry 116 further includes a trender 214, which generates, for a particular parameter, a trend of measurement values over time, for example, based on the information stored in the measurement memory 212 and/or other information. The measurement memory 212 also stores the trends.

The self-diagnostic circuitry 116 further includes logic 216. The logic 216 analyzes a measurement and/or trend for one or more of the parameters based on the information stored in the measurement memory 212 and/or other information. The self-diagnostic circuitry 116 further includes rules 218 and criteria 220. The logic 216, based on the analysis and the rules 218 and criteria 220, generates a signal indicative of a result of the analysis, and, in the illustrated embodiment, conveys the signal to the console 122. The signal can also be conveyed to another component and/or stored in the measurement memory 212 and/or other memory.

The rules 218, generally, instruct the logic 216 based on the analysis result. In one instance, this includes instructing the logic 216 to estimate when service should be performed based on information provided in the rules 218. For example, a rule may indicate that for a particular value and/or trend for a particular parameter, the imaging detector should be serviced within in X time period. Another rule may indicate that a service flag should be set in a particular manner based on the particular value and/or trend for the particular parameter.

The self-diagnosing circuitry 116 further includes criteria 220, which provide analysis criteria for the logic 216. The criteria 220 includes information as to how a measurement and/or a trend will be analyzed. For example, the criteria 220 may include a predetermined threshold value and/or a predetermined range of values. In another example, the criteria 220 may indicate that historical data from the measurement memory 212 be used. The historical data includes the calibration and/or previous measurements and/or benchmarks and/or other information.

The console 122, in response to receiving the signal, may display a notification (in human readable format) indicating service for and/or a health state of the detector module $112_I$ (e.g., re-calibration and/or replacement, degradation of performance, lifetime issues, defect, etc.). The notification may also include the particular measured parameter, along with the measured value and/or a trend of the measured value and an acceptable range for the parameter.

The console self-diagnostic software application may also send a service request, e.g., over a network, to a remote service computer, in response thereto. The service request may include the trend and/or a suggested time frame in which service should be performed. This information may be used to adjust an already planned service and/or schedule a new service. Of course, the service request may also be ignored, discarded, and/or otherwise not used.

Figure 3:
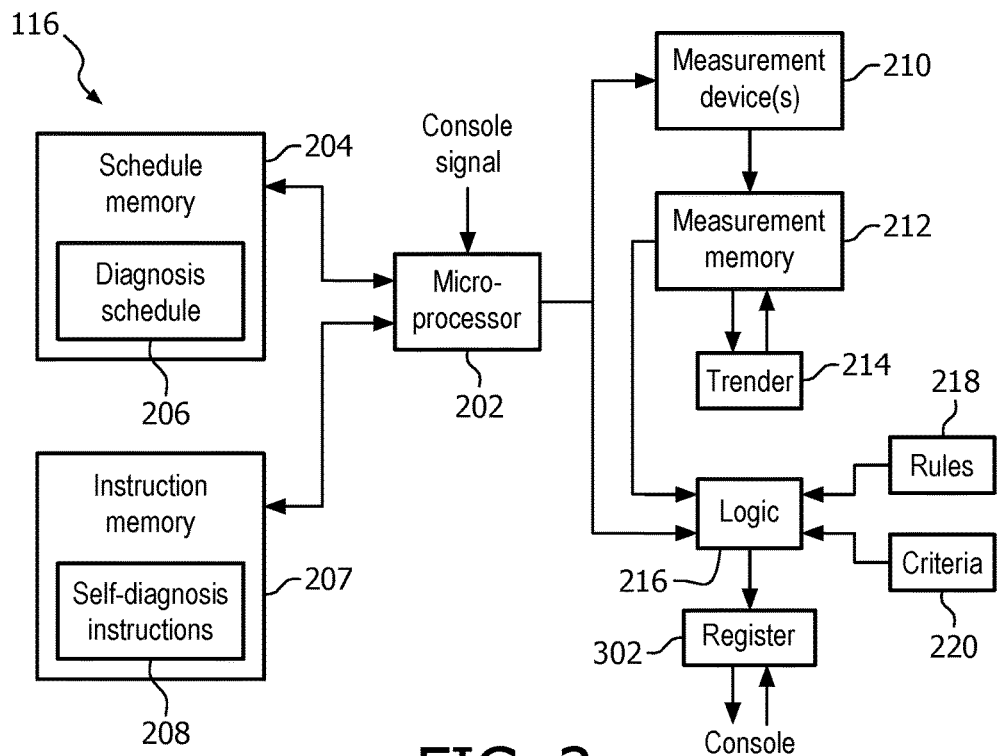

FIG. 3 schematically illustrates a variation of FIG. 2.

In this variation, the self-diagnosing circuitry 116 additionally includes a register 302. The logic 216, based on the analysis, sets a bit in the register 302. The bit indicates whether a particular parameter satisfies the criteria 220, whether service should be performed, etc., where the rules 218 instruct the logic 216 with setting the bit.

For example, setting a bit to one (1) may indicate the parameter satisfies the criteria 220 and setting a bit to zero (0) may indicate the parameter does not satisfy the criteria 220, or vice versa. Alternatively, setting a bit to one (1) may indicate service is not needed and setting a bit to zero (0) may indicate the service is needed or will be needed soon, or vice versa. A larger number of bits may be used to indicate further information such as the measured parameter value, the service date estimate, etc.

In a variation, the logic 216, based on the analysis, sets multiple bits in the register 302 for a particular parameter. For example, in one instance, the register could be a counter, and each time a particular event occurs corresponding to the particular parameter, the counter is incremented to count that event. In this configuration, the register 302 identifies a number of occurrences of an event. Other bits may be used to indicate further information such as the measured parameter value, the service date estimate, etc.

The microprocessor 202, in one instance, pushes or conveys the one or more bit values of the register 302 to the console 122. In another instance, the console 122 periodically polls or reads the one or more bit values of the register 302. In another instance, a remote service application or client receives the one or more bit values of the register 302 and/or reads the one or more bit values of the register 302.

In variation, the self-diagnostic circuitry 116 can also diagnose components of the imaging system 100 external to the detector module $112_I$. For example, the self-diagnostic circuitry 116 can also be used to diagnose the radiation source 108, a source collimator 124, a high voltage generator 126, and/or other components external to the detector module $112_I$. This may include evaluating a radiation profile to identify incorrect collimation and thus a defective source collimator 124, the energy of the incident beam to identify potential radiation source 108, high voltage generator 126, or radiation source control issues, etc. This information, similar to the information about the detector module $112_I$, can be processed by the detector module $112_I$ and/or processing components external to the detector module $112_I$.

Figure 4:
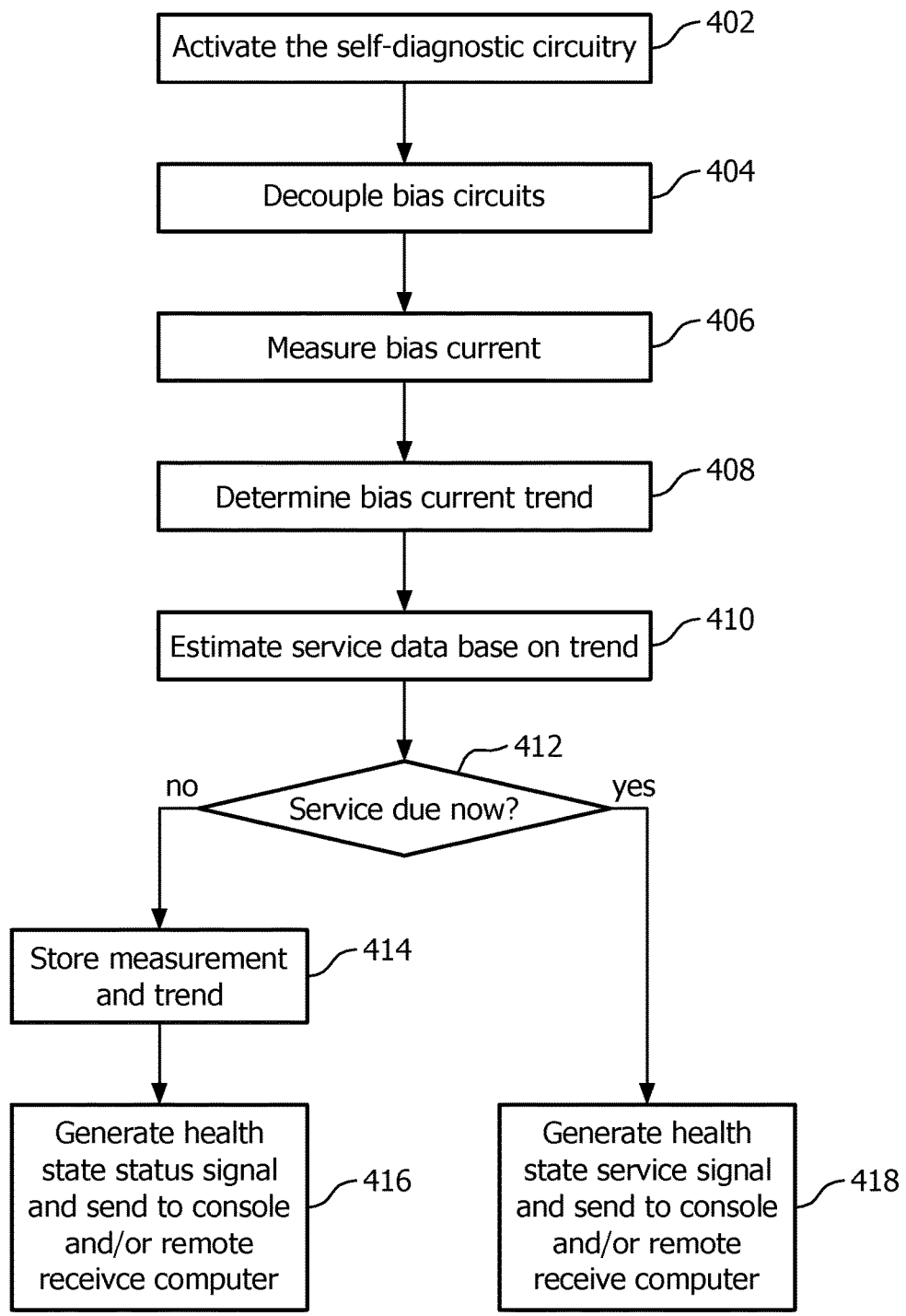
FIG. 4 illustrates an example method for diagnosing a health of a detector module with self-diagnostic circuitry of the detector module and generating and conveying a signal indicating an estimated date of service for the module.

FIG. 4 illustrates an example method for diagnosing a health of a detector with self-diagnostic circuitry of the detector.

For sake of brevity and clarity, the example method of FIG. 4 is described with respect to measuring an electrical current of a bias circuit. However, it is to be understood that other parameters, such as those described herein as well as other parameters can be monitored.

It is to be appreciated that the ordering of the acts of these methods is not limiting. As such, other orderings are contemplated herein. In addition, one or more acts may be omitted and/or one or more additional acts may be included.

At 402, the self-diagnostic circuitry 116 is activated.

At 404, a bias circuit of a detector module is electrically decoupled.

At 406, a bias current of the bias circuit is measured.

At 408, a bias current trend over time is generated. For example, a degradation slope can be calculated as a ratio of a change in the bias current to a change in time.

At 410, an estimated date of service is estimated based on the trend.

At 412, it is determined whether service is due now based on the estimated date of service.

If service is not due now, then at 414, the measurement and/or trend is stored, and at 416, the estimated date of service is conveyed to the console 122 or a remote service computer.

If service is due now, then at 418, a signal indicating service is required is conveyed to the console 122 or a remote service computer.

Again, the above method is a non-limiting. This particular method does not require any additional components and/or signals. However, other approaches may utilize additional components. For example, in a variation, an optical component such as a light emitting diode (LED) can be integrated into the detector and illuminate with a predefined sequence to indicate performance of and/or outcomes of self-tests for crosstalk, sensitivity, linearity, etc.

In another approach, an external electrical current pulse is injected into detector, for example, to access drift in connection with a threshold scan amplitude. This allows for assessing whether the drift measured is caused by the ASIC. This may include measuring an internal current source to isolate if changes in gain are caused by radiation dose effects on a test circuitry, and measuring internal nodes of the ASIC (bias currents).

In another approach, a number of counts above a threshold and its evolution with time are assessed. This may be an indication of material degradation and/or readout electronics radiation dose effects. This can be done by measuring a threshold scan and assess the position of the baseline peak and measuring directly the leakage current suing an on-asic current ADC.

Figure 5:
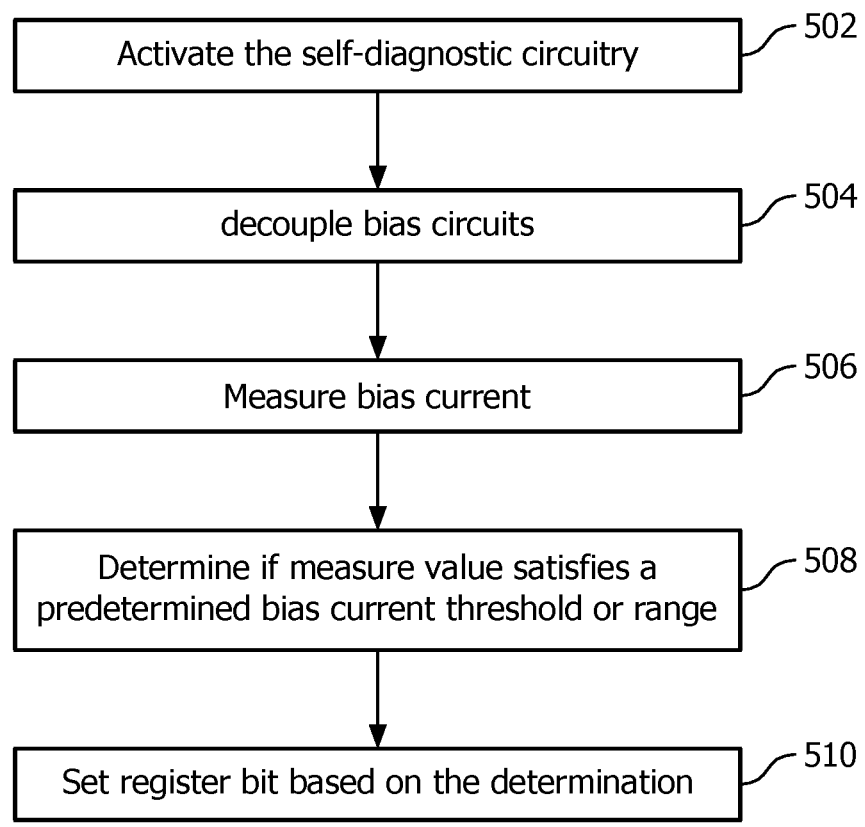
FIG. 5 illustrates an example method for diagnosing a health of a detector module with self-diagnostic circuitry of the detector module and setting a register bit indicative thereof.

FIG. 5 illustrates an example method for diagnosing a health of a detector module with self-diagnosing circuitry of the detector module.

For sake of brevity and clarity, the example method of FIG. 5 is described with respect to measuring an electrical current of a bias circuit. However, it is to be understood that other parameters, such as those described herein as well as other parameters can be monitored.

It is to be appreciated that the ordering of the acts of these methods is not limiting. As such, other orderings are contemplated herein. In addition, one or more acts may be omitted and/or one or more additional acts may be included.

At 502, the self-diagnostic circuitry 116 is activated.

At 504, a bias circuit of a detector module is electrically decoupled.

At 506, a bias current of the decoupled bias circuit is measured.

At 508, it is determined whether the measured bias current satisfies a predetermined bias current threshold or range.

At 510, a bias current register bit is set based on a result of the determination.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

The invention claimed is:

1. A Computer Tomography imaging detector module of a Computed Tomography imaging system, comprising:
   at least one detector pixel; and
   self-diagnosing circuitry, including:
      a microprocessor; and
      at least one measurement device,
   wherein the microprocessor is configured to control the at least one measurement device to measure at least one parameter of the at least one detector pixel, wherein a value of the at least one parameter is indicative of a health state of the imaging system;
   the self-diagnosing circuitry, further comprising:
      a trender that is configured to generate a trend for the parameter, wherein the trend is to indicate measurement values for the lease one parameter over time;
      a logic that is configured to analyze the trend in view of predetermined criteria and to generate a signal based on a result of the analysis.

2. The Computer Tomography imaging detector module of claim 1, wherein the signal is to include an estimated service date for at least the imaging detector module based on a result of the analysis.

3. The Computer Tomography imaging detector module of claim 2, wherein a service schedule for the imaging detector module is to be created based on the signal.

4. The Computer Tomography imaging detector module of claim 3, wherein the logic sets the bit a second different value of the multiple possible values in response to the measured at least one parameter not satisfying the predetermined criteria.

5. The Computer Tomography imaging detector module of claim 1, wherein the signal is to indicate a particular type of service for the imaging detector module based on a result of the analysis.

6. The Computer Tomography imaging detector module of claim 1, wherein the signal is to include the parameter and the criteria.

7. The Computer Tomography imaging detector module of claim 1, wherein the service indicates at least one of repair, replacement, calibration, or software correction.

8. The Computer Tomography imaging detector module of claim 1, the self-diagnosing circuitry, further comprising:
   a register; and
   a logic that is configured to compare the measured at least one parameter with predetermined criteria and sets a bit in the register based on a result of the comparison.

9. The Computer Tomography imaging detector module of claim 8, wherein the logic is configured to set the bit to a first value of multiple possible values in response to the measured at least one parameter satisfying the predetermined criteria.

10. The Computer Tomography imaging detector module of claim 1, further comprising:
    a schedule memory that is configured to store a diagnosis schedule, wherein the microprocessor is configured to control the at least measurement device to measure the at least one parameter based on the diagnosis schedule.

11. The Computer Tomography imaging detector module of claim 10, wherein the at least measurement device includes at least two measurement devices, each configured to measure a different parameter, wherein the diagnosis schedule includes a different self-diagnosis schedule for each of the at least two measurement devices.

12. The Computer Tomography imaging detector module of claim 1, wherein the at least one measurement device includes one or more sensors configured to sense one or more of detector bias current, detector dark current, detector gain, detector noise, detector sensitivity, detector homogeneity, detector crosstalk, or detector temperature.

13. A computed tomography imaging system comprising:
    a console that controls a scanning operation of the imaging system;
    a radiation source that emits radiation the traverse an examination region; and
    a detector array that detects radiation traversing the examination region, the detector array, including:
       a detector module, the detector module, including:
          at least one detector pixel; and
          self-diagnosing circuitry,
       wherein the self-diagnosing circuitry measures at least one parameter of the at least one detector pixel, generates imaging detector service related information for the imaging detector based on the measured at least one parameter, generates a signal including the information, and conveys the signal to the console, which visually displays a notification including the information.

14. A method, comprising:
    employing self-diagnosing circuitry embedded in Computer Tomography imaging detector module of Computer Tomography imaging system to measure at least one parameter of at least one detector pixel of the imaging detector module,
    wherein a value of the at least one parameter is Indicative of a health state of the Computer Tomography imaging detector; and
    generating, with the self-diagnosing circuitry, a signal indicating a health state of the Computer Tomography imaging detector module based on the measured at least one parameter;
    generating trend for the at least one parameter, wherein the trend indicates measurement values for the least one parameter over time;
    comparing the trend to pre-determined criteria; and
    predicting a next service date for the imaging detector module based on a result of the comparison and pre-determined rules.

15. The method of claim 14, wherein a second value of the at least one parameter is indicative of a second health state of a component external to the imaging detector module, and the signal further indicates the second health state of the component.

16. The method of claim 14, wherein the signal includes an estimated service date for the imaging detector based on the measured at least one parameter.

17. The method of claim 16, wherein the notification further includes at least one of a type of service to be performed and the measured at least one parameter.

18. The method of claim 14, further comprising:
    conveying the signal to a remote service computing system.

* * * * *